United States Patent [19]

Wedekamp

[11] Patent Number: 5,200,156

[45] Date of Patent: Apr. 6, 1993

[54] DEVICE FOR IRRADIATING FLOWING LIQUIDS AND/OR GASES WITH UV LIGHT

[75] Inventor: Horst Wedekamp, Herford, Fed. Rep. of Germany

[73] Assignee: Wedeco Gesellschaft fur Entkeimungsanlagen mbH, Herford, Fed. Rep. of Germany

[21] Appl. No.: 477,934

[22] PCT Filed: Oct. 25, 1989

[86] PCT No.: PCT/DE89/00691

§ 371 Date: Jul. 16, 1990

§ 102(e) Date: Jul. 16, 1990

[87] PCT Pub. No.: WO90/04454

PCT Pub. Date: May 3, 1990

[30] Foreign Application Priority Data

Oct. 26, 1988 [DE] Fed. Rep. of Germany ....... 3836494

[51] Int. Cl.$^5$ .............................................. B01J 19/12
[52] U.S. Cl. .................................... 422/186.3; 422/24; 313/493; 313/634
[58] Field of Search ................. 422/186.3, 186, 24; 204/157.15, 158.2; 250/436, 455.1, 432 R, 435, 438; 313/24, 36, 493, 634

[56] References Cited

U.S. PATENT DOCUMENTS

| 3,634,025 | 1/1972 | Landry | 21/102 |
| 3,637,342 | 1/1972 | Veloz | 21/102 |
| 3,657,087 | 4/1972 | Scott | 204/158 R |
| 4,214,962 | 7/1980 | Pincon | 204/157.1 |
| 4,323,810 | 4/1982 | Horstmann | 313/24 |
| 4,952,376 | 8/1990 | Peterson | 422/186.3 |

Primary Examiner—Donald P. Walsh
Assistant Examiner—Daniel Jenkins
Attorney, Agent, or Firm—Collard & Roe, P.C.

[57] ABSTRACT

A device for irradiating flowing liquids and/or gasses with ultraviolet (UV) light comprising a casing with in and outlet apertures and one or more UV light sources wherein the light sources are within protective tubes. The light sources are arranged such that the maximum radiation occurs along the axis of flow of the liquid and/or gasses.

15 Claims, 3 Drawing Sheets

DEVICE FOR IRRADIATING FLOWING LIQUIDS AND/OR GASES WITH UV LIGHT

BACKGROUND

The invention relates to a device pursuant to the preamble of Claim 1 as well as pursuant to the preamble of Claim 12.

Such devices intended for irradiating media with UV light are generally known. In this connection, the wish is that the devices for irradiating media with UV light be more effective in their treatment effect than possible chemical methods, with the same economic efficiency. This presupposes a high UV light/space/time yield with the lowest possible energy and apparatus expenditure.

For implementation of these devices, a combination between the irradiation space and the UV light source arrangement is generally striven for, in which each volume element of the medium is irradiated with the same UV dose, to the greatest extent possible. The ideal case to achieve the highest degree of effectiveness consists of having the average dose be equal to the minimum dose. To achieve this goal, the following criteria must be optimized:
1. avoiding radiation losses;
2. achieving the most uniform irradiation intensity possible;
3. achieving the most uniform contact time and/or flow velocity possible.

The prerequisites pursuant to Numbers 2 and 3 can often only be fulfilled by means of complicated auxiliary equipment for swirling up the medium to be sterilized or treated.

The invention is based on the task of improving a device for irradiating flowing liquids and/or gases with UV light, so that radiation losses are reduced, in order to achieve the most uniform irradiation intensity possible, and furthermore so that uniform contact times can be achieved, all with a simple structure.

Pursuant to a first alternative, this task is accomplished with the characterizing features of Claim 1, for the device stated in the preamble of Claim 1.

The new device is designed for installation in a pipeline, and has a new type of radiation distribution for this purpose, with which the criteria mentioned above can be fulfilled to a great extent. The use of a pipeline means that a pressure system is involved, in which the medium (liquid and/or gases) is passed through the pipeline by means of pressure.

Optionally, either a single or several quartz protective pipes, each equipped with a rod-shaped UV light source, are arranged in the center of the housing and perpendicular to the flow direction of the medium. Whether one or several UV light sources are used depends on the desired throughput amount. For high throughput performance, a greater number of UV light sources is used, arranged next to one another and in a maximum of two rows. If arranged in two rows, the UV light sources are offset relative to one another in the flow direction of the medium.

The UV light sources preferably have a flat oval cross-section and special radiation characteristics, as well as higher electrical outputs, in comparison with known UV light sources with a round cross-section. For a flat emitter—in other words for a UV light source with a flat oval cross-section—the radiation flow is emitted ¾ via the broad side and only ¼ via the narrow side. Radiation via the broad side also is much more bundled than for UV light sources with a round cross-section. The UV light sources emit greater than 50% of their emitted light via the broad side flat walls, and lesser than 50% via the narrow side oval walls.

This results in UV emission with the maximum directed towards the two flat sides. By arranging one or several UV light sources (flat emitters) in a plane perpendicular to the flow direction and adjacent to the connection openings of the housing or the connected pipeline, the maximum of the UV emission reaches the connected pipeline with the radiation going essentially parallel, specifically reaching both the inflowing and the outflowing medium in equal parts.

Since the upstream and downstream pipeline is supposed to run in a straight line with the radiation direction, the radiation can penetrate into the medium without loss, i.e. until it is completely absorbed. This has not been the case with the devices known until now.

Although a device for sterilization of liquids is known from Austrian Patent 362 076, in which a radiation loss is prevented to a great extent by using reflectors, a large part of the radiation is still lost after it passes through the irradiation chamber.

Such disadvantages of the known devices are eliminated with the device according to the invention (which is also designated as a UV light barrier). Due to its construction and the directed distribution of radiation, wall losses are equalized to a great extent. With a high density of rays, an almost homogeneous distribution of radiation in the medium to be treated, as well as transfer of the radiation flow with little loss, i.e. almost complete absorption of the UV emission in the medium, is guaranteed.

Due to the directed and essentially parallel alignment of the UV emission, the mathematical limit case of an expansive level source of rays is approached, and the weakening of irradiation intensity with an increasing distance from the source of the rays, caused due to geometry, is avoided to a great extent.

Since the flow direction and the radiation direction are parallel, it follows that the dose applied to one volume element of the medium results from the quotient of the irradiation intensity and the flow velocity of the medium, integrated over the entire length of the pipeline.

The dependence of the dose applied on the distance to the axis must be taken into consideration by multiplication with the ratio of the radial distribution of the irradiation intensity and velocity. Spacial differences in the irradiation intensity in the axial direction are therefore equalized by taking the average across the path of the volume element. With this taking of the average, the dependence of the irradiation intensity on the axial distance to the source of the rays is eliminated. A high degree of uniform distribution of the dose applied to each volume element is the result.

The radial distribution of the irradiation intensity possesses a flat maximum in the center of the pipe, and weakens as it approaches the edge of the pipe. The radial distribution of the velocity has a similar profile. Model calculations show that the quotient of both distribution functions is constant within ±10% over the entire pipe cross-section, depending on the flow velocity and the emitter arrangement.

In a device according to the invention, in contrast to conventional UV irradiation systems, for the first time the same UV dose is applied to each volume element, within a variation range of a few percentage points.

Computer simulations have shown the exemplary performance capacity of a device according to the invention, as shown in the table below, taking into consideration marginal effects, changes in cross-section, UV transmission of water as well as the arrangement of the UV light sources. The table shows a calculated comparison of the performance capacity of a known device, with a according to the invention (at a dose of 35 mWs/cm$^2$).

| Device | Prior Art | Invention |
| --- | --- | --- |
| Number of UV emitters | 4 | 5 |
| effective UV output (254 nm) | 184 W | 158 W |
| throughput: | | |
| T (1 cm) = 96% | 80 m$^3$/h | 106 m$^3$/h |
| T (1 cm) = 90% | 59 m$^3$/h | 74 m$^3$/h |

Device according to the invention: diameter of the pipeline 250 mm; net cross-section 511 cm$^2$. Reactor volume for the known device: 31 liters.

A device according to the invention is characterized by a degree of effectiveness that is approximately 50% higher than that of a conventional device with the emitter arrangement in the flow direction.

The directed radiation of the UV emission, the arrangement of the UV light sources relative to one another and perpendicular to the flow direction, as well as the adapted housing shape of the device, result in a degree of effectiveness previously not achieved in the transfer of UV light radiation to the medium to be treated, which cannot be achieved with devices known until now.

A special advantage of the invention is that the new device is suited for being subsequently installed in an existing pipeline, with the device simply being inserted as an intermediate piece.

Pursuant to another alternative, the task on which the invention is based is accomplished with the features indicated in the characterizing section of Claim 12, for a device according to the preamble of Claim 12.

Here, there is no pipeline, and instead, a flume through which liquid flows, such as those used in sewage treatment plants, is used.

In other words, this is a pressure-free system, with the flume being understood as a housing open towards the top.

This form of a solution also results in the advantages for sterilization of liquids by means of UV radiation that is directed and extends in a straight line in the direction of the flume, which is also in a straight line, as described above, Preferably, several UV light sources brought together in one or even several rows can be structured as a kind of emitter module, which is easy to handle and therefore can also be simply inserted into the flume from above. If needed, several such emitter modules can be placed into the flume at certain intervals from one another.

In the following, the invention is explained in more detail on the basis of the embodiments shown in the drawing. This shows:

PREFERRED EMBODIMENT OF THE INVENTION

Figure 1:
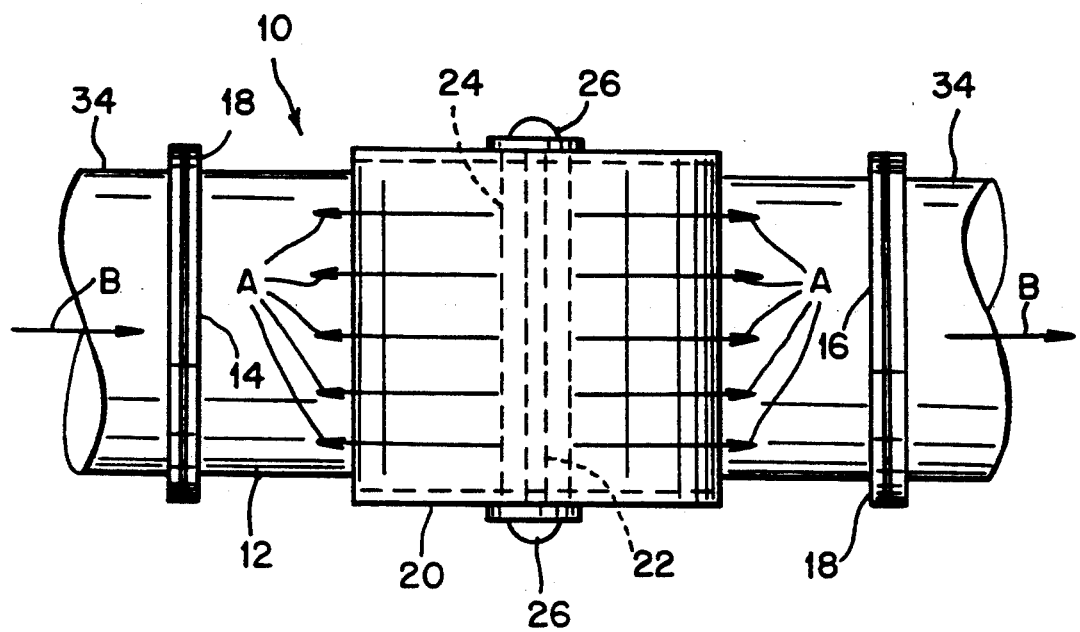
FIG. 1: a schematic view of a device placed in a pipeline.
Figure 2:
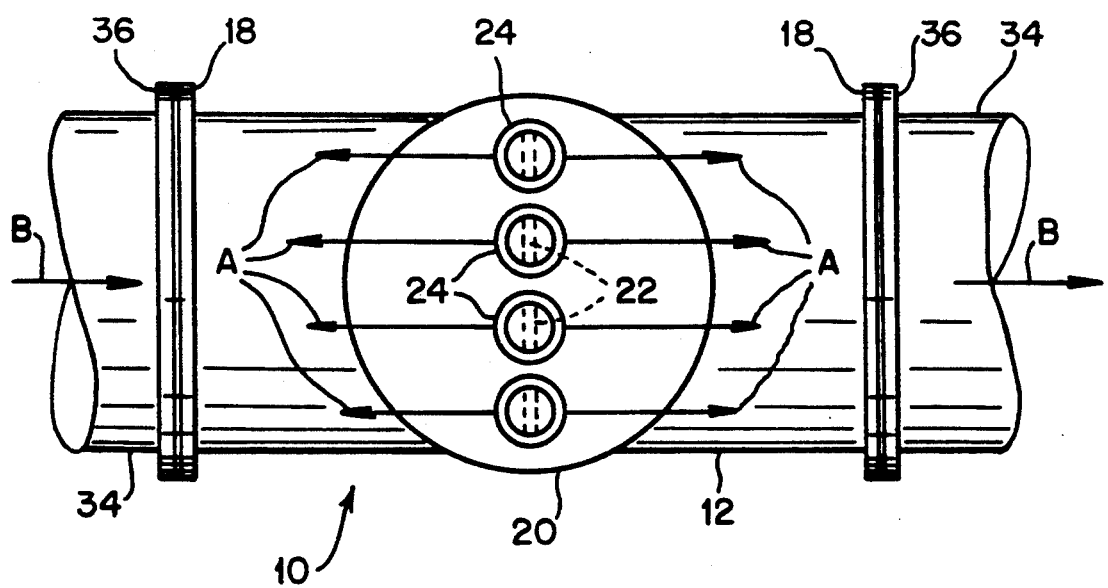
FIG. 2: a top view of the device according to FIG. 1.

According to FIG. 1 and 2, a device 10 with UV light sources 22 is inserted in a pipeline 34, through which a liquid flows in the direction of the arrows B. The device 10 is connected via the two housing connectors 18 and the related pipe connectors 36.

The device 10 with its housing 12 has a holder device 20, which carries four UV light sources arranged in a row, perpendicular to the flow direction B, which are structured as flat emitters with a flat oval cross-section and are each surrounded by a protective pipe 24. The electrical connections 26 of the flat emitters 22 run outside of the holder device 20. Flat oval cross-section means that there are two parallel flat walls a spaced distance apart with oval walls connecting together the end of the flat walls across the spaced distance.

A liquid which flows in the pipeline 34 in the flow direction B gets into the housing 12 of the device through an entry opening 14, and the liquid flows off via the right part of the pipeline 34, through an exit opening 16. The liquid therefore flows through the housing 12 with the flat emitters 22, which are arranged in a row, perpendicular to the flow direction B.

Because of its known property, each flat emitter 22 produces radiation with a preferred radiation direction A. The maximum of the UV light emission is therefore directed and extends in the flow direction and opposite the flow direction B of the liquid. Therefore the UV radiation can extend beyond the housing 12 into the pipeline 34, which runs in a straight line, at both sides of the device 10. The housing 12 and the pipeline 34 each have the same cross-section, in this case.

Figure 3:
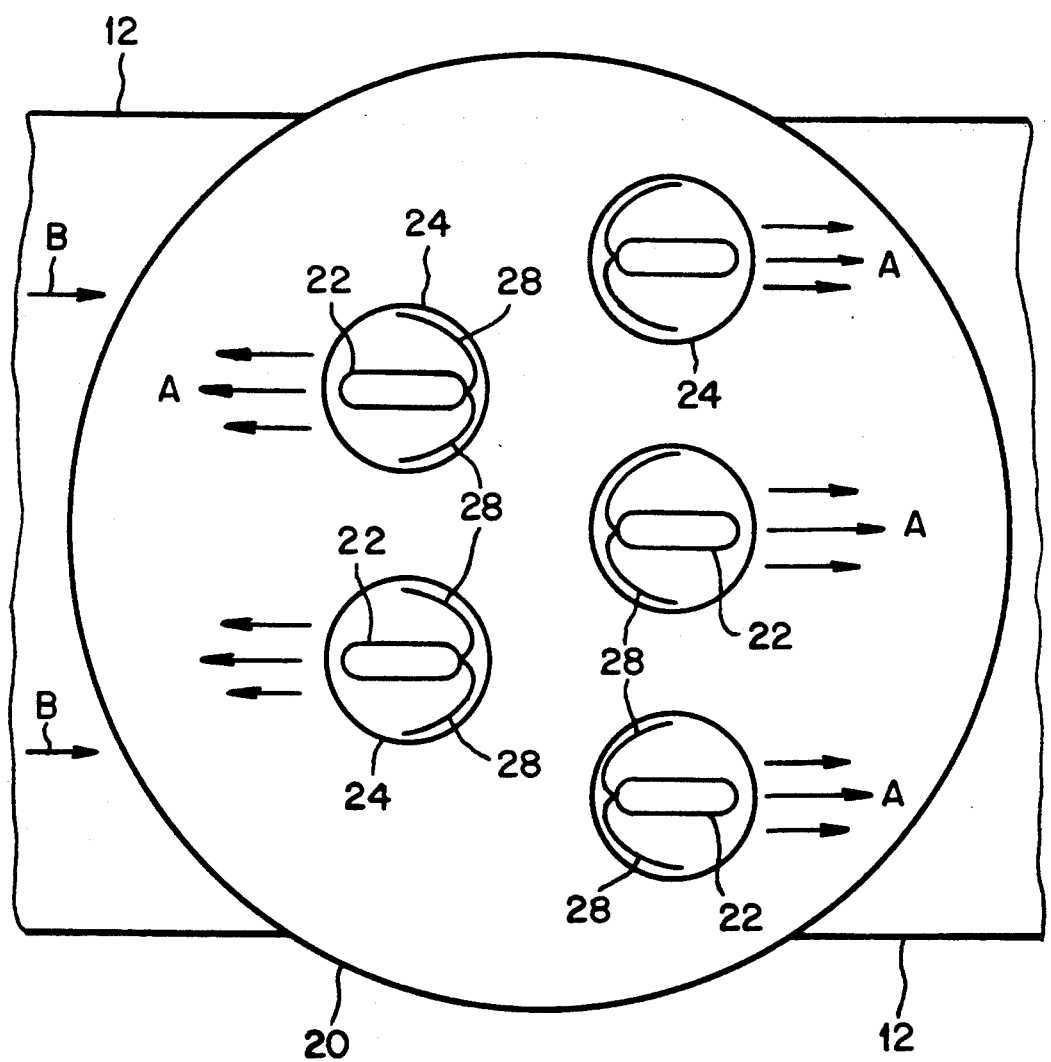
FIG. 3: a schematic view of another device, with two rows of UV light sources with reflectors.

In the embodiment of a device according to the invention as shown in FIG. 3, two rows of UV light sources 22 arranged perpendicular to the flow direction B are provided; these are equipped with reflectors 28 to support and improve directed emission A. With these reflectors 28, the radiation of the individual flat emitters is deflected and influenced in such a way that they give off directed radiation either only to the left or only to the right, to a greater degree, as indicated with the arrows A in FIG. 3. As a matter of principle, other types of reflectors are also possible, and UV light sources with a round cross-section can also be used, in which directed radiation can be produced by using suitable reflectors. It should be noted for the flat emitters 22 shown in FIG. 3 that here, their broad sides extend not perpendicular but parallel to the flow direction B, because optimum directed UV light emission A can be achieved by this, in combination with the reflectors 28.

Figure 4:
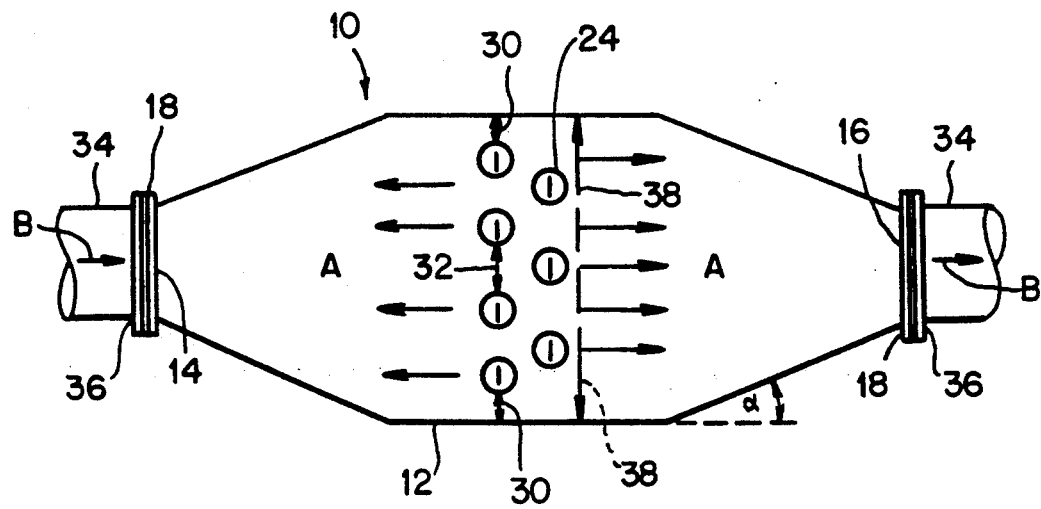
FIG. 4: another embodiment, in which the housing cross-section of the device decreases in the direction of the connector points of the pipeline.

FIG. 4 shows an embodiment in which the housing cross-section 38 is greater in the center, in the area of the flat emitters 22, than the cross-section of the connected pipeline 34. With this measure, the dwell time of the liquid within the housing 12 can be increased, which results in even better sterilization. The conical reduction in size of the housing cross-section 38 towards the two housing connections 18 preferably takes place at an angle α that is not greater than 45°. Furthermore, the ratio of the housing cross-section 38 to the cross-section of the connected pipeline 34 is selected to be no greater than 1:1.5. With these limits, especially excellent results can be achieved.

The following measures are also advantageous. The distance 30 evident in FIG. 4, between the protective pipe of the outer UV light sources 22 of a row and the housing wall of the housing 12 is sized to be so small so that the irradiation intensity of the radiation directed at the housing wall still amounts to approximately 50% of the irradiation intensity produced by the UV light source in question. Furthermore, the distances 32 between the protective pipes of the adjacent UV light sources 22 are selected to be at least twice as great as the aforementioned distances 30.

The flat emitters 22 emit their maximum not only in the direction A, but also perpendicular to the flow direction B, although to a significantly lesser extent. By sizing the distances 30 and 32 as indicated, this ensures that sufficient irradiation intensity exists even between the adjacent UV light sources, in other words that the medium which flows past here is still subjected to the UV radiation to the desired degree.

The devices pursuant to FIG. 1-4 described until now relate to a structure with a pipeline. This involves a so-called pressure system, in which the liquid is passed through the pipeline 34 and the housing 12 of the device 10 under pressure.

Figure 5:
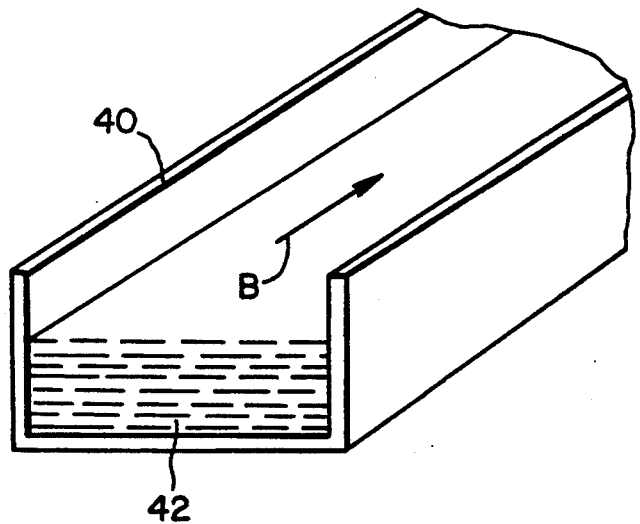
FIG. 5: a perspective view of a flume.

However, the invention can also be used advantageously with pressure-free systems. For this, FIG. 5 shows a flume 40, open to the top, as used in sewage treatment plants, which has the shape of a ditch and through which a liquid 42 flows.

Figure 6:
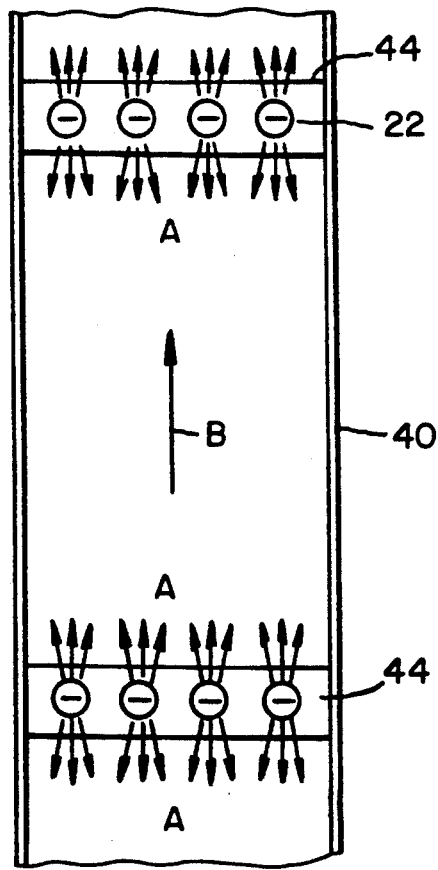
FIG. 6: a top view of the flume according to FIG. 5, with emitter modules placed in it.

An emitter module 44, which comprises several flat UV emitters arranged in a row perpendicular to the flow direction, can be inserted into such a pressure-free system with a flume 40 in simple manner, according to the invention, as shown in FIG. 6.

The flat UV emitters 22 dip into the liquid 42 with their usual protective pipes. Once again, the UV light emission A is directed, and its maxima extend in the directions B of the inflowing and outflowing liquid 42.

If necessary, several emitter modules 44 can be used at intervals from one another.

What is claimed is:

1. A device for irradiating a flowing liquid or gas medium with UV light, comprising
   a housing with an upstream entry opening for inflowing medium and with a downstream exit opening for out-flowing medium; and
   one or several UV light sources arranged in protective pipes which are permeable for UV light, said UV light sources located within said medium and arranged in such a way that the UV light radiation is directed and its maximum extends in the flow direction of the inflowing medium and the outflowing medium;
   wherein the UV light sources have a flat oval cross-section;
   said flat oval cross-section comprising two parallel flat walls with oval walls connecting together the ends of said flat walls;
   and wherein said UV light sources emit greater than 50% of their emitted light via said flat walls, and lesser than 50% via said oval walls; and
   said flat walls oriented perpendicular to the direction of flow of said liquid or gas medium.

2. A device for irradiating a flowing liquid or gas medium with UV light, comprising
   a housing with an upstream entry opening for inflowing medium and with a downstream exit opening for outflowing medium;
   one or several UV light sources arranged in protective pipes which are permeable for UV light, said UV light sources located within said medium and arranged in such a way that the UV light radiation is directed and its maximum extends in the flow direction of the inflowing medium and the outflowing medium;
   wherein the UV light sources for production of a directed radiation distribution and increased density of rays have a flat oval cross-section;
   said flat oval cross-section comprising two parallel flat walls a spaced distance apart with oval walls connecting together ends of said flat walls across said spaced distance;
   said flat walls oriented parallel to the direction of flow of said liquid or gas medium; and
   protective pipes with light-deflecting ribbing or light reflectors that so surround said flat walls and said oval walls whereby said UV light sources emit greater than 50% of their emitted light via said flat walls, and lesser than 50% via said oval walls.

3. The device pursuant to claim 2.
   wherein several UV light sources are inserted next to one another in one or several rows, perpendicular to the flow direction.

4. The device pursuant to claim 3,
   wherein said housing has lateral walls; and
   the distances between the housing lateral walls of the device and the next UV light source is kept small enough so that the irradiation intensity along this distance does not increase by more than 50%.

5. The device pursuant to claim 4,
   wherein when several UV light sources are used, the distances between the UV light sources of one row relative to one another are at least twice as great as the distances to the housing lateral walls of the housing of the device.

6. The device pursuant to claim 5,
   wherein the entry opening has a cross-section, the exit opening has a cross-section, the housing has a cross-section; and
   wherein the cross-section of the entry opening and the cross-section of the exit opening is equal to the cross-section of the housing.

7. The device pursuant to claim 6,
   wherein the cross-section of the entry opening and the cross-section of the exit opening is half as great as the total cross-sectional area which results from the free passages or distances between the individual UV light sources with their protective pipes as well as the distances to the housing lateral walls.

8. The device pursuant to claim 6,
   wherein the cross-section of the housing is greater than the cross-section of the entry opening and the cross-section of the exit opening; and
   wherein the housing cross-section at the two ends of the housing decreases to the cross-section of the entry opening and the cross-section of the exit opening.

9. The device pursuant to claim 8, wherein one pipeline is connected to the entry opening and another pipeline is connected to the exit opening;

wherein the housing cross-section decreases conically, with the ratio of the housing cross-section in the center, where it is not decreased, to the pipelines which are connected at the end with an unchanged radius, being no greater than 1:1.5, and that the decrease angle $\alpha$ being no greater than 45°.

10. The device pursuant to claim 9,
wherein the pipelines for the medium to be treated extend in the directions of the maximum light radiation of the UV light sources.

11. The device pursuant to claim 1,
wherein said UV light source is a temperature-stabilized UV light source.

12. A device for irradiating a flowing liquid or gas medium with UV light comprising
a housing with an entry opening for an inflowing medium and an exit opening for an outflowing medium;
one or several UV light sources arranged in protective pipes which are permeable for UV light radiation;
said housing is structured as an open housing in the shape of a flume through which said liquid medium flows; and
said UV light radiation is directed and its maximum occurs in the direction of the inflowing medium and the direction of the outflowing medium;
wherein the UV light source have a flat oval cross-section;
said flat oval cross-section comprising two parallel flat walls with oval walls connecting together the ends of said flat walls;
and wherein said UV light sources emit greater than 50% of their emitted light via said flat walls and lesser than 50% via said oval walls; and
said flat walls oriented perpendicular to the direction of flow of said liquid or gas medium.

13. The device pursuant to claim 12,
wherein several UV light sources are inserted next to one another in one or several rows, perpendicular to the flow direction with the UV light sources being comprised as a unit, to form an emitter module.

14. The device pursuant to claim 12,
wherein emitter modules are inserted at intervals along the flume.

15. A device for irradiating a flowing liquid or gas medium with UV light comprising
a housing with an entry opening for an inflowing medium and an exit opening for an outflowing medium;
one or several UV light sources arranged in protective pipe which are permeable for UV light radiation;
said housing is structured as an opening housing in the shape of a flume through which said liquid medium flows;
said UV light radiation is directed and its maximum occurs in the direction of the inflowing medium and the direction of the outflowing medium;
wherein the UV light sources have a flat oval cross-section;
said flat oval cross-section comprising two parallel flat walls with oval walls connecting together the ends of said flat walls;
said flat walls oriented parallel to the direction of flow of said liquid or gas medium; and
protective pipes with light-deflecting ribbing or light reflectors that so surround said flat walls and said oval walls whereby said UV light sources emit greater than 50% of their emitted light via said flat walls, and lesser than 50% via said oval walls.

* * * * *